(12) United States Patent
Ostan et al.

(10) Patent No.: US 11,285,050 B2
(45) Date of Patent: Mar. 29, 2022

(54) MEDICAL DRESSING

(71) Applicant: MOLNLYCKE HEALTH CARE AB, Gothenburg (SE)

(72) Inventors: Karin Ostan, Nodinge (SE); Angelica Andresen, Kungsbacka (SE); Malin Martensson, Boras (SE); Patrick Rodzewicz, Gothenburg (SE)

(73) Assignee: MÖLNLYCKE HEALTH CARE AB, Gothenburg (SE)

( * ) Notice: Subject to any disclaimer, the term of this patent is extended or adjusted under 35 U.S.C. 154(b) by 423 days.

(21) Appl. No.: 15/622,367

(22) Filed: Jun. 14, 2017

(65) Prior Publication Data

US 2017/0367898 A1     Dec. 28, 2017

(30) Foreign Application Priority Data

Jun. 23, 2016 (EP) .................................... 16176005

(51) Int. Cl.
*A61F 13/02*  (2006.01)
*A61F 13/06*  (2006.01)
*A61F 13/00*  (2006.01)

(52) U.S. Cl.
CPC .......... *A61F 13/064* (2013.01); *A61F 13/023* (2013.01); *A61F 13/066* (2013.01); *A61F 13/069* (2013.01); *A61F 13/0203* (2013.01); *A61F 13/0263* (2013.01); *A61F 2013/00817* (2013.01)

(58) Field of Classification Search
CPC ...... A61F 13/06; A61F 13/069; A61F 13/063; A61F 2013/15024; A61F 2013/00089; A61F 2013/00387; A61F 2013/00604; A61F 2013/00404; A61F 13/068; A61F 2013/00574; A61F 2013/00578;

(Continued)

(56) References Cited

U.S. PATENT DOCUMENTS

| 4,266,298 A | 5/1981 | Graziano |
| 5,704,905 A * | 1/1998 | Jensen ................ A61F 13/0259 602/42 |

(Continued)

FOREIGN PATENT DOCUMENTS

| CN | 1764426 A | 4/2006 |
| CN | 101500520 | 8/2009 |

(Continued)

OTHER PUBLICATIONS

EP16176005.3 Extended European Search Report dated Nov. 3, 2016.

(Continued)

*Primary Examiner* — Rachael E Bredefeld
*Assistant Examiner* — Brant T Bennett
(74) *Attorney, Agent, or Firm* — Kilpatrick Townsend & Stockton LLP

(57) ABSTRACT

A medical dressing having a geometrical plane of symmetry. A border portion extends along the contour of the pad. A central portion of the dressing has a smaller width perpendicular to the plane of symmetry than the widths of the adjoining portions. The medical dressing comprises a gripping tab which is coplanar with the border portion and which projects outwardly from the border portion. The medical dressing may be used for pressure ulcer prevention, such as at a heel of a human body.

21 Claims, 6 Drawing Sheets

(58) Field of Classification Search
CPC .. A61F 13/02–0206; A61F 2013/00451; A61F 13/0203; A61F 13/0263
USPC .............................. 604/304–306; 602/41–59
See application file for complete search history.

(56) References Cited

U.S. PATENT DOCUMENTS

| | | | |
|---|---|---|---|
| 7,091,394 B2* | 8/2006 | Kolte | A61F 13/0203 602/42 |
| 7,820,875 B2* | 10/2010 | Roe | A61F 13/51466 604/378 |
| 7,858,838 B2* | 12/2010 | Holm | A61F 13/0203 602/58 |
| 8,715,211 B1* | 5/2014 | Prandini | A61F 5/30 602/11 |
| 9,877,872 B2* | 1/2018 | Mumby | A61F 13/0203 |
| 2006/0206047 A1* | 9/2006 | Lampe | A61F 13/105 602/42 |
| 2014/0249495 A1 | 9/2014 | Mumby et al. | |

FOREIGN PATENT DOCUMENTS

| | | |
|---|---|---|
| CN | 101965169 | 2/2011 |
| CN | 102196790 | 9/2011 |
| CN | 103857365 A | 6/2014 |
| CN | 204501232 | 7/2015 |
| DE | 69612256 T2 | 8/2001 |
| JP | 2010500124 A | 1/2010 |
| JP | 2004513704 A | 5/2013 |
| JP | 2014523778 A | 9/2014 |
| WO | 0239940 A2 | 5/2002 |
| WO | 2002039940 A2 | 5/2002 |
| WO | 2008019310 A1 | 2/2008 |
| WO | 2013007973 A2 | 1/2013 |

OTHER PUBLICATIONS

Application No. CN 201780039061.0, Office Action dated Aug. 25, 2020, 12 pages.
Application No. CN 201780039061.0, Office Action dated Dec. 2, 2020, 11 pages.
Australian Application No. 2017282674, Examination report No. 1 for standard patent application, dated Jun. 17, 2021, 4 pages.
CN 2018-567135, Notice of Reasons for Rejection dated Aug. 3, 2021, 6 pages (with English-language translation, 10 pages).

* cited by examiner

MEDICAL DRESSING

CROSS-REFERENCE TO RELATED APPLICATIONS

The present application claims priority to European Patent Application No. 16176005.3, filed Jun. 23, 2016, which is incorporated herein by reference in its entirety.

TECHNICAL FIELD

The present disclosure relates to a medical dressing for application on the heel of a human body.

BACKGROUND ART

Pressure ulcers very often arise among persons being bedridden for various reasons, such as for instance due to long term hospitalization or other causes of immobility. Not only does a pressure ulcer cause great discomfort and/or pain to the affected person, but it also causes difficulties to nursing personnel and other care-takers.

It is therefore desirable in, for instance, hospitals to act proactively rather than reactively. In other words, instead of waiting for pressure ulcers to develop and then perform treatment, it is preferred to try to prevent the pressure ulcers from even occurring.

Pressure ulcers are largely preventable. When pressure ulcers occur, they can become painful wounds that require months to heel. The prevention of pressure ulcers includes inspection of the skin, control of risk factors, keeping the skin clean and dry, and redistributing pressure over high risk bony areas.

To date, such preventative means typically include pressure off-loading or re-positioning the patient at regular intervals such that pressure is relieved or re-distributed, and the amount of pressure that the individual is exposed to is minimized.

Where a pressure sore has started to develop, or where it is expected to develop, nursing personnel may place a padded dressing onto the skin area. The nursing personnel needs to check from time to time to examine the skin underneath the dressing, and to see if a pressure ulcer has developed.

The inspection of the skin area requires the dressing to be opened up, and detached from the skin. One option is, of course, to remove the dressing and apply a new dressing after having checked the relevant skin area. However, this is both costly and time consuming. Alternatively, nursing personnel may detach the dressing slightly by gripping and lifting an adhesive border of the dressing (i.e. the portion of the dressing surrounding the pad) so that the relevant skin area can be checked, and then the dressing is re-applied by re-attaching the adhesive border to the surrounding skin. Although this is cost effective and less time consuming than removing the old dressing and applying a new dressing, there are some drawbacks.

One drawback is that there is a risk that the border will become wrinkled when detached and re-applied, which reduces the adhesive capacity. Additionally, there is a risk that such wrinkles turn into compartments for body fluids (such as sweat) which in turn may lead to such compartments growing as more fluid is accumulated, therefore further reducing the stay-on ability of the dressing. Eventually, the nursing personnel will, due to the resulting reduced stay-on ability, need to replace the old dressing with a new one.

Some areas of the human body have a higher risk of developing pressure ulcers than other areas. For instance, the heel is such a sensitive area of the human body. The anatomy and physiology of the heel make the tissue very vulnerable to pressure. When pressure is increased in high risk patients, such as those with peripheral arterial disease and neuropathy, the risk of ulceration and failure to heal is greatly increased. Patients at risk of increased pressure on the heel are those who cannot move their legs, such as patients who are anaesthetized, paralyzed, or have undergone orthopaedic injury or surgery. These patients require additional precautions to prevent heel ulceration. While pressure causes compression of the tissue, shear forces occur between the layers of the tissue and tend to tear and separate them. In some cases, this results in blister formation and breakdown of the fibers that hold the layers of fat and collagen together.

Applying a dressing to the heel for pressure ulcer preventing purposes may be challenging, since it includes covering parts of the foot sole as well as the lateral and medial sides of the foot, resulting in numerous directions and planes of extensions for the adhesive border of the dressing. This further increases the challenge for the nursing personnel, who needs to decide where to detach the border for enabling inspection and yet being able to re-apply the border adequately after inspection.

SUMMARY OF THE INVENTION

An object of the present disclosure is to alleviate the drawbacks of the prior art. This and other objects, which will become apparent in the following are accomplished by the accompanying claims.

The present disclosure is based on the realization that by providing a medical dressing with a narrowing central region (forming a waist) and also providing the medical dressing with a gripping tab, a synergetic effect is achieved. The detaching and adequatate re-applying of the medical dressing becomes easier, even for challenging body areas such as the heel, and the nursing personnel will also have a guide with respect to where to start detaching the medical dressing. Adequate detaching and re-applying of the medical dressing results in longer stay-on ability of the medical dressing and less frequent need for replacing an old dressing with a new one. Thus, the present invention provides for beneficial technological and economical progress in the field of pressure ulcer prevention.

According to at least one aspect of this disclosure, there is provided a medical dressing. The medical dressing comprises
a pad having a geometrical plane of symmetry,
a substantially planar border portion extending along the contour of the pad, the border portion forming a peripheral edge of the medical dressing, wherein the medical dressing comprises:
  a first portion having a first width,
  a second portion having a second width, and
  a third portion having a third width,
wherein each one of the first, second and third widths extends from a respective point of the peripheral edge on one side of the plane of symmetry to a respective point of the peripheral edge on the other side of the plane of symmetry, and wherein each one of the first, second and third widths extends perpendicularly to the plane of symmetry,
  wherein the third portion is located between and adjoining to the first portion and the second portion,
  wherein the third width is smaller than each one of the first width and the second width, wherein the medical dressing comprises a gripping tab which is coplanar with the border portion and which projects outwardly from the border portion.

The medical dressing is particularly useful for pressure ulcer prevention and/or pressure ulcer mitigation. Furthermore, the configuration of having a wider first and second portions, and a narrower third portion in between, makes the medical dressing particularly suitable for pressure ulcer prevention/mitigation at the heel of a human body.

Although is some embodiments, at least one of the first, second and third portions may have a substantially constant width, in other embodiments at least one of the first, second and third portions may have varying width.

According to at least some exemplary embodiments, the third width is the maximum width of the third portion. Thus, according to at least some exemplary embodiments, the maximum width of the third portion is smaller than a width of the first portion and also smaller than a width of the second portion. Thus the third portion will form a narrow portion, such as a waist, of the product, since it is adjoining to the first and second portions.

According to at least some exemplary embodiments, the first width is the maximum width of the first portion, the second width is the maximum width of the second portion, and the third width is the maximum width of the third portion. Thus, according to at least some exemplary embodiments, the maximum width of the third portion is smaller than the maximum width of the first portion and also smaller than the maximum width of the second portion.

According to at least some exemplary embodiments, the first width is the minimum width of the first portion, the second width is the minimum width of the second portion, and the third width is the maximum width of the third portion. Thus, according to at least some exemplary embodiments, the maximum width of the third portion is smaller than the minimum width of the first portion and also smaller than the minimum width of the second portion.

According to at least some exemplary embodiments, the medical dressing has a longitudinal extension in a longitudinal direction coinciding and running in parallel with the geometrical plane of symmetry, and a lateral extension in a lateral direction running perpendicularly to the geometrical plane of symmetry, wherein the gripping tab projects from the border portion at least in the longitudinal direction so that no other part of the medical dressing extends beyond the gripping tab in the longitudinal direction. This provides a clearly discernable and accessible gripping tab for the nursing personnel. The exemplary embodiments may also be expressed mathematically. For instance, in an orthogonal coordinate system having Cartesian coordinates (x, y, z), the lateral direction could correspond to the x-direction, while the longitudinal direction could correspond to the y-direction (and the thickness of the medical dressing would extend in the z-direction). Thus, with such Cartesian coordinates the gripping tab would constitute the outermost part of the medical dressing as seen in the y-direction.

According to at least some exemplary embodiments, the border portion circumferentially surrounds the contour of the pad, i.e. the border portion may form a closed path around the contour of the pad. However, in other exemplary embodiments the path of the border portion along the contour of the pad may be broken. For instance, at the third portion of the medical dressing the border portion may be omitted, and in such case the pad is suitably sealed, for instance by welding, to avoid pad material (such as absorbent material) to fall out from the pad.

According to at least some exemplary embodiments, the gripping tab is made in one piece with the border portion. This is practical from a manufacturing perspective. However, other alternatives such as separate gripping tabs attached to the border portion are also conceivable.

The gripping tab may suitably be located at one of the first and second portions. The medical dressing may, suitably be provided with more than one gripping tab. For instance, there may be two gripping tabs. In some embodiments having at least two gripping tabs, a first tab may be located on one side of the plane of symmetry and a second tab may be located on the other side of the plane of symmetry. Such first and second tabs, may suitably be located symmetrically with respect to the plane of symmetry. Both tabs may, for instance be located at the first portion, or at the second portion. However, it is also conceivable to have a first tab at the first portion and a second tab at the second portion, wherein such first and second tabs may either be located on the same side of the plane of symmetry or on different sides (i.e. diagonally) of the plan of symmetry.

According to at least some exemplary embodiments there may be more the two gripping tabs, for instance three or four gripping tabs. In embodiments having four gripping tabs, two of the tabs may be at the first portion of the dressing, one on each side of the plan of symmetry, and similarly two of the tabs may be at the second portion of the dressing.

According to at least some exemplary embodiments, the one or more gripping tabs, is/are coated with an adhesive layer for adhering the tab to skin surrounding the area of prevention. This may be advantageous to avoid accidental removal forces being applied to the gripping tab/tabs, bearing in mind that a gripping tab is more likely to rise relative to the rest of the product if it is not adhered to the skin. If the gripping tab is formed in one piece with the border portion, it may also be advantageous from a manufacturing point of view to share the adhesive layer of a body contact layer of the border portion.

Assuming the medical dressing would be circumscribed by an imaginary rectangle, then the four tabs would suitably be located in the corners of the rectangle.

Regardless of if one, two, three or four gripping tabs are present on a medical dressing according to embodiments of this disclosure, each gripping tab is suitably coplanar with the border portion and is suitably made in one piece with and projecting outwardly from the border portion. In this connection it should be understood that inwardly means a direction towards the inner perimeter of the border portion, i.e. a direction towards the pad, while outwardly is an opposite direction.

According to at least one exemplary embodiment, the medical dressing comprises a backing layer and an adhesive body contact layer, wherein the pad is arranged between the backing layer and the body contact layer, wherein the backing layer and the body contact layer extend beyond the periphery of the pad to define the border portion, which extends along the contour of the pad.

In the field of medical dressings, in particular, wound dressings, a film provided with an adhesive layer for adhering to the patient is often referred to as a wound contact layer. The present disclosure is primarily intended for pressure ulcer prevention, i.e. for use on a human body area which has no wound. Therefore, in this application the combined film and adhesive layer will be referred to as a body contact layer. However, it should be understood that although the primary use of this disclosure is pressure ulcer prevention, if nursing personnel decides to use it as a wound dressing the body contact layer could be applied onto a wound.

According to at least some exemplary embodiments, the pad may suitably be an absorbent pad for absorbing moisture or body exudates. In some embodiments, the body contact layer may be partially (e.g. centrally or peripherally) or completely omitted, in which case the backing layer may be coated with an adhesive layer for attachment to the skin.

In this application directional terms such as "proximal" or "proximally" and "distal" or "distally" are used. These terms are referenced with respect to the intended placement on a human body. In other words, the most proximal portion of the medical dressing is the portion that is intended to be nearest the human body. The most distal portion is the portion that is intended to be furthest away from the human body. For instance, the adhesive layer will be proximal to the film.

According to at least one exemplary embodiment, the adhesive body contact layer comprises a film coated with an adhesive layer. Suitably, the the adhesive layer may cover at least 75% of the surface of the film. The adhesive layer can be considered to be provided on a body-facing proximal side of the film. If the border portion is formed by both the body contact layer and a backing layer, then the backing layer is attached to the opposite distal side of the film of the body contact layer.

Suitably, the adhesive layer covers at least 90%, for example substantially the entire surface of the film. The adhesion to the skin is thereby enhanced, which improves the stay-on ability of the dressing. It also aids in reducing the friction between the skin the patient and the dressing surface, when a person slides or moves his heels in bed. This way, the skin is prevented from stretching.

According to at least one exemplary embodiment, the border portion has a bending length of at least 32 mm as measured by the test method SS-EN ISO 9073-7:1998, and suitably a tensile strength of between 3.5 and 10 N, preferably between 4 and 6 N at an elongation of 25%, as measured by ASTM D 882-12. These characteristics are important for inspection of the skin. A caregiver must regularly inspect the skin to study any differences in skin appearance, which may indicate that a pressure ulcer is about to develop. In order to improve the handling; i.e. the application and re-application of the dressing onto the skin, it is important that the border portion has sufficient rigidity such that it does not curl or folds against itself during inspection. At the same time, it must not be too rigid as it should be able follow and conform to contoured surfaces of the skin, e.g. the sacrum. Therefore, the drapeability (i.e. the bending length), and the tensile strength are important factors and should be carefully balanced.

According to at least one example embodiment, the film of the body contact layer is a perforated film. The perforations in the film may form a regular pattern. This allows any body exudates or other moisture to be transported away from the skin. According to at least one example embodiment the film coated with the adhesive layer is a plastic film. Suitable materials for the plastic film include, but are not limited to breathable polyolefin-based films (such as, e.g. polyethylene), polyamide, polyurethane, polyester and silicone. The film may have a thickness of from 15 to 100 μm, e.g. from 30 to 70 μm, e.g. from 45 to 60 μm. Suitably, the film is a thin polyurethane film.

According to at least one example embodiment, the adhesive layer comprises a hydrophobic material. Examples of suitable adhesives include, but are not limited to, silicone gels, hot melt adhesives, acrylate adhesives, polyurethane gels, and hydrocolloid adhesives. In some embodiments, the adhesive is comprised of a material that is non-irritating to skin, for example, a silicone gel. Examples of suitable silicone gels include the two-component RTV systems such as Q72218 (Dow Corning) and SilGel 612 (Wacker Chemie AG) mentioned herein, as well as the NuSil silicone elastomers. In embodiments of this disclosure, the adhesive may comprise a silicone gel. For example, the adhesive may comprise a soft silicone gel having as softness (penetration) of from 8 to 22 mm, such as for example from 12 to 17 mm, as measured by a method based on ASTM D 937 and DIN 51580.

According to at least one example embodiment, the medical dressings comprises a release layer, intended to be removed before use. The release layer may be disposed on and releasably attached to the proximal side of the body contact layer. By "releasably attached," it is meant that the release layer may be peeled away from the rest of the medical dressing by hand. The release layer acts as a barrier that can protect the sterility of the pad and any adhesive (such as the adhesive layer) present on the proximal surface of body contact layer (and any adhesive present on the backing layer and pad depending on their extension relative to the body contact layer) before the dressing is used. The release layer may be made of any of a variety of suitable materials known in the art, such as, for example, polyethylene, polyester, polypropylene, and silicone-coated paper.

According to at least one exemplary embodiment, the backing layer may typically be a thin film, sheet, or membrane that is vapor permeable and waterproof. Examples of suitable materials for the backing layer include, but are not limited to breathable polyurethane, polyester, polyethylene or polyamide films, silicone films, polyester-based nonwoven materials, and laminates of polyester-based nonwoven materials and polyurethane films. The backing layer may be bonded to the pad and/or the body contact layer (i.e. the film coated with an adhesive layer on the proximal side), for example, via an adhesive such as a pressure sensitive adhesive (such as an acrylic adhesive). In at least some embodiments, the backing layer is co-extensive with the body contact layer in that both layers have the same outer dimensions, and is bonded to the distal side of the film in the border portion of the medical dressing.

According to at least one example embodiment, the pad comprises a material that provides for good pressure distribution and fluid handling. For example, the pad may comprise an absorbent, conformable material such as, for example, foams and/or cellulose-based materials. The pad may comprise a hydrophilic material, e.g., a hydrophilic foam. Suitable foam materials include, but are not limited to polyurethane foams. In some embodiments, the pad comprises a porous foam. In some embodiments, the pad is a multilayered pad. For example, the pad may comprise two or more layers having different properties laminated together. For example, the pad can comprise a first absorbent layer on its proximal side and a second absorbent layer on its distal side, with the second absorbent layer being affixed to the backing layer. In some such embodiments, another layer is disposed between the first absorbent layer and the second absorbent layer, for example, a liquid distributing layer, which can act to spread liquid absorbed by the first absorbent layer and transmit the liquid to the second absorbent layer. In some embodiments, the first absorbent layer is comprised of a foam, for example, a hydrophilic foam such as a hydrophilic polyurethane foam. In some embodiments, the second absorbent layer comprises a superabsorbent material, such as superabsorbent fibers (SAF) or superabsorbent polymers (SAP). For example, polyacrylic super-absorbent fibers may be suitable. The second absorbent layer may also comprise binding fibers, non-limiting examples of which include polyester fibers, polyethylene fibers, polypropylene fibers, and blends thereof. Alternatively or additionally, the second absorbent layer may comprise cotton fibers. In some embodiments, the liquid distributing layer is thinner than both the first and second absorbent layers. In some embodiments, the liquid distributing layer is comprised of a nonwoven material, such as, for example, viscose, polyester, or both.

As can be understood from the above disclosure, in at least some exemplary embodiments, the medical dressing comprises a backing layer and a body contact layer. In such embodiment, any gripping tab or gripping tabs may be formed by at least one of the backing layer and the adhesive body contact layer. In at least some exemplary embodiments, the gripping tab or gripping tabs may be formed by both the backing layer and the adhesive body contact layer, the backing layer being affixed to the distal side of the adhesive body contact layer. This provides gripping tab having a sandwiched structure. Thus, the backing layer may be attached to the film of the adhesive body contact layer, a portion (or portions) of these combined layers forming a gripping tab (or tabs) projecting outwardly from the border portion.

Suitably, the backing layer may extend uninterrupted from the pad to the gripping tab.

While a gripping tab having a sandwiched structure provides increased rigidity and control of handling, such benefits may also be achieved by designing the individual layers with properly dimensioned thickness. Thus, in at least some embodiments the gripping tab is only formed by the adhesive body contact layer (or its film), in which case the gripping tab projects beyond the backing layer. In some embodiments, the medical dressing may be provided without any body contact layer, or at least without any body contact layer in the border portion, wherein the backing layer may suitably be provided with an adhesive coating and the gripping tab may be formed by the backing layer.

According to at least one exemplary embodiment, on each side of the plane of symmetry, the pad is provided with a respective wedge-shaped indentation between the first portion of the dressing and the second portion of the dressing, forming a waist of the pad at the third portion of the dressing. This is particularly advantageous for applying the medical dressing to a heel. In some embodiments the border portion may be void of corresponding indentations. However, according to at least some exemplary embodiments, on each side of the plane of symmetry, the border portion is provided with a respective wedge-shaped indentation between the first portion of the dressing and the second portion of the dressing, forming a waist of the border portion at the third portion of the dressing. This allows for an advantageous application of the border portion to a heel.

Although in some embodiments only one of the pad and border portion has the wedge shaped indentations, in other embodiments both the pad and the border portion have wedge-shaped indentations between the first portion of the dressing and the second portion of the dressing, forming waists of the pad and of the border portion respectively at the third portion of the dressing. In such cases, the wedged-shaped indentation of the pad may be (slightly) displaced relative to the wedge-shaped indentation of the border portion. Suitably, the wedge-shaped indentation of the pad may be displaced more towards the first portion, while the wedge-shaped indentation of the dressing may be displaced more towards the second portion.

According to at least one exemplary embodiment, on each side of the plane of symmetry, the pad has a first substantially linear rim portion extending from the third portion of the dressing to the first portion of the dressing and a second substantially linear rim portion extending from the third portion of the dressing to the second portion of the dressing. The above mentioned wedge-shaped indentations of the pad may, suitably, be at least partly defined by the first and second substantially linear rim portions of the pad. In some embodiments, one or both of the first and second substantially linear rim portions may transit into other portions which may also form part in defining the wedge-shaped indentations of the pad.

According to at least some exemplary embodiments, an angle of 50°-70°, suitably 55°-65°, is formed between the directions of extension of the first and second rim portions. This is particularly advantageous in the case of the medical dressing being applied to a heel. To protect the relevant parts of the heel any gap formation at those parts should be avoided. If a gap is formed, the pressure ulcer preventing/mitigating capacity of the medical dressing will be largely reduced. The above indicated angle range between the first and second substantial linear rim portions of the pad is suitable for avoiding gap formation when the medical dressing is placed on a heel. A too large angle would most likely result in a gap.

The first and the second substantially linear rim portions may suitably be asymmetrically located with respect to an imaginary line between the two, extending perpendicularly to the plane of symmetry. It has been found that such an asymmetry between the first and second substantially linear rim portions is advantageous because it allows the medical dressing to be placed on a heel in a sufficiently satisfactory manner even if the nursing staff would slightly misplace the medical dressing relative to what would be considered the desired application position of the medical dressing.

The above described asymmetry of the first and second linear rim portions is reflected in at least some exemplary embodiments, wherein an angle of 0°-20° is formed between the direction of extension of the first substantially linear rim portion and an imaginary geometric line, the imaginary geometric line extending between the first and second substantially linear rim portions and extending perpendicularly to the plane of symmetry. Consequently, this implies that in cases for which the full angle between the directions of extension of the first and second rim portions is 50°-70°, the angle between the imaginary geometric line and the direction of extension of the second substantially linear rim portion would be in the range of 30°-70° (e.g. 30°-50° if the full angle is at the lowest value, i.e. 50°, or 50°-70° if the full angle is at the highest value, i.e. 70°). From this it may be understood that the wedge-shaped indentation may suitably be displaced more towards the second portion than towards the first portion of the medical dressing.

According to at least one exemplary embodiment, on each side of the plane of symmetry, each one of the first substantially linear rim portions has an inner end located closest to the plane of symmetry and an outer end located farthest from the plane of symmetry, wherein the outer end of the first substantially linear rim portion on one side of the plane of symmetry and the outer end of the first substantially linear rim portion on the other side of the plane of symmetry are separated from one another by a distance of 9-16 cm, suitably 10-12 cm. This too reduces the risk of misplacing the medical dressing at, for instance, a heel, and avoids gap formation. A separating distance below 9 cm will risk the formation of gaps when the medical dressing is applied to a normal-sized adult heel. A separating distance larger than 16 cm would result in a bulky medial dressing because of too much material. The separating distance is normally measured perpendicularly to the plane of symmetry.

According to at least one exemplary embodiment, the pad has a smallest width in a direction perpendicular to the plane of symmetry, the smallest width being in the range of 3-4.5 cm. It should be understood that smallest the width of the pad is normally located at the third portion of the medical dressing. Such a smallest width is advantageous in that the pad will in an applied position around a heel have no or only little excess material bulging away from the heel. For a normal adult foot, all or most of the pad will follow the contour of the heel. Thus, the risk of bulkiness and forming of sharp edges due to folds in the pad are greatly reduced.

The combination of thin waist at the third portion (i.e. a low value for the smallest width of the pad) and a strong widening of the pad into the first portion provides an advantageous fit of the pad to a heel. Not only does the narrow smallest width avoid formation of bulky parts in the applied state of the medical dressing, but the strong widening allows for good protection on the heel edges and reducing the risk of gap formation. Such widening is reflected in at least one exemplary embodiment, according to which the first portion of the medical dressing has, at a distance of 1 cm from the smallest width (Ws) of the pad, an increased width (Wi), the distance of 1 cm being measured along the pad and the plane or axis of symmetry, wherein both Ws and Wi are measured perpendicularly to the plane of symmetry, wherein the increase $$\frac{Wi - Ws}{Ws}$$

is in the range of 100%-300%, suitably in the range of 150%-250%. For instance, if Ws is 3 cm and Wi is 12 cm, the increase will be 300%; if Ws is 4.5 cm and Wi is 9 cm, the increase will be 100%; if Ws is 3.5 cm and Wi is 10 cm, the increase will be 186%, and so on.

According to at least one exemplary embodiment, the medical dressing is substantially butterfly-shaped. The border portion may thus form an outer contour which substantially resembles to a butterfly-shape. It should noted that part of the pad, may at least partly follow the same contour. For instance in some exemplary embodiments, in the first portion of the medical dressing the pad may substantially conform to the shape of the border portion, while in the second portion of the medical dressing, the pad may have the same or a different shape compared to the border portion. For instance, in the second portion of the medical dressing the pad may have the shape of a truncated triangle with two rounded corners.

In the case of the medical dressing being substantially butterfly-shaped, the first portion may form a first pair of wings and the second portion may form a second pair of wings, wherein each one of the first and second pairs has one wing on one side of the plane of symmetry and another wing on the other side of the plane of symmetry. Such wing portions allows for an advantageous application onto a heel of a human body.

According to at least one exemplary embodiment, a recess is formed between the pair of wings. Suitably the recess may be defined by a substantially U-shaped path of the border portion and/or the pad.

According to at least one exemplary embodiment, the pad follows a substantially U-shaped path from one of the wings of the first pair of wings to the other one of the wings of the first pair of wings. In other words, at the first portion of the medical dressing, the lateral parts of the pad extend further away from the third portion of the medical dressing than the central part of the pad does at the first portion of the medical dressing. This allows the lateral parts of the pad (forming part of the first pair of wings) at the first portion of the medical dressing to extend all the way to and protect the malleoli of a human foot. Suitably, the border portion may have a similar contour. Thus, according to at least one exemplary embodiment, the contour of the border portion follows a substantially U-shaped path from one of the wings of the first pair of wings to the other one of the wings of the first pair of wings.

The above mentioned substantially U-shaped paths of the pad and/or the border portion may suitably be such that the legs of the U-shape are directed obliquely relative to the plane of symmetry.

Although a substantially U-shaped path between the first pair of wings has been suggested above, the configuration of the first pair of wings may be defined differently for at least some exemplary embodiments. According to at least some exemplary embodiments, the pad has a geometrical axis of symmetry coinciding with the plane of symmetry, the axis of symmetry defining an axial direction, wherein the first portion of the dressing comprises an (first) intermediate portion which extends from one of the wings of the first pair of wings, across the plane of symmetry, to the other one of the wings of the first pair of wings, wherein, seen in the axial direction, each one of the wings of the first pair of wings extends beyond the (first) intermediate portion such that in a direction perpendicular to the plane of symmetry, a void is present between the first pair of wings. Suitably, both the pad and the border portion is present in the first pair of wings so that, at the first pair of wings, both the pad and the border portion extend beyond the (first) intermediate portion.

For at least some exemplary embodiments, a similar definition is applicable to the second portion of the medical dressing. Thus, according to at least some exemplary embodiments, the pad has a geometrical axis of symmetry coinciding with the plane of symmetry, the axis of symmetry defining an axial direction, wherein the second portion of the dressing comprises an (second) intermediate portion which extends from one of the wings of the second pair of wings, across the plane of symmetry, to the other one of the wings of the second pair of wings, wherein, seen in the axial direction, each one of the wings of the second pair of wings extends beyond the (second) intermediate portion such that in a direction perpendicular to the plane of symmetry, a void is present between the second pair of wings.

As has been explained above, according to at least some exemplary embodiments, the medical dressing may have more than one gripping tab. For configurations including the above mentioned first and second pairs of wings, it has been found particularly advantageous to provide gripping tabs on the second pair of wings, as these will normally be the ones that the nursing staff will lift from the skin first, when checking for pressure ulcer development. This is reflected in at least some exemplary embodiments, according to which the gripping tab is a first gripping tab projecting outwardly from the border portion of one of the wings of the second pair of wings, wherein the medical dressing further comprises a second gripping tab projecting outwardly from the border portion of the other one of the second pair of wings.

Suitably, in case of more than one gripping tab are present, the entire medical dressing may have a plane of symmetry. For instance, two tabs may be located as mirror images with respect to each other on either side of such a plane of symmetry. This is reflected in at least one exemplary embodiment of this disclosure, according to which the border portion has a geometrical plane of symmetry which coincides with the plane of symmetry of the pad. The gripping tab is typically made in one piece with, and projecting outwardly from the border. The gripping tab may be made of the same materials as the border portion, e.g. it may be made from the backing layer and the body contact layer. Alternatively, the gripping tab may be reinforced by an additional material layer, e.g. a nonwoven or a film to make the tab stiffer and easier to grasp. In embodiments, the entire border portion, or at least parts thereof may be reinforced by applying an additional material portion at the border portions. The gripping tab may be covered by the adhesive body contact layer. It is also conceivable to have no adhesive layer underneath the gripping tab of the dressing. The gripping tab may be of a variety of shapes, including square, rectangular, triangular, or rounded. The size and the dimensions of the gripping tab may also be adjusted. The gripping tab should be be sized to be easy to grip with a thumb and another finger. In the case of a rounded or semicircular gripping tab, the radius may be in the range of 5 mm to 20 mm, e.g. 8 mm to 15 mm. According to at least one exemplary embodiment the surface area of the or each gripping tab is between 0.4 and 6 cm$^2$, suitably between 1 and 3.5 cm$^2$. The size of the tab is of course dependent on the size of the dressing. The tab should be of a size that guides the user to see it, and to grasp it properly for inspection.

DETAILED DESCRIPTION OF THE DRAWINGS

Figure 1:
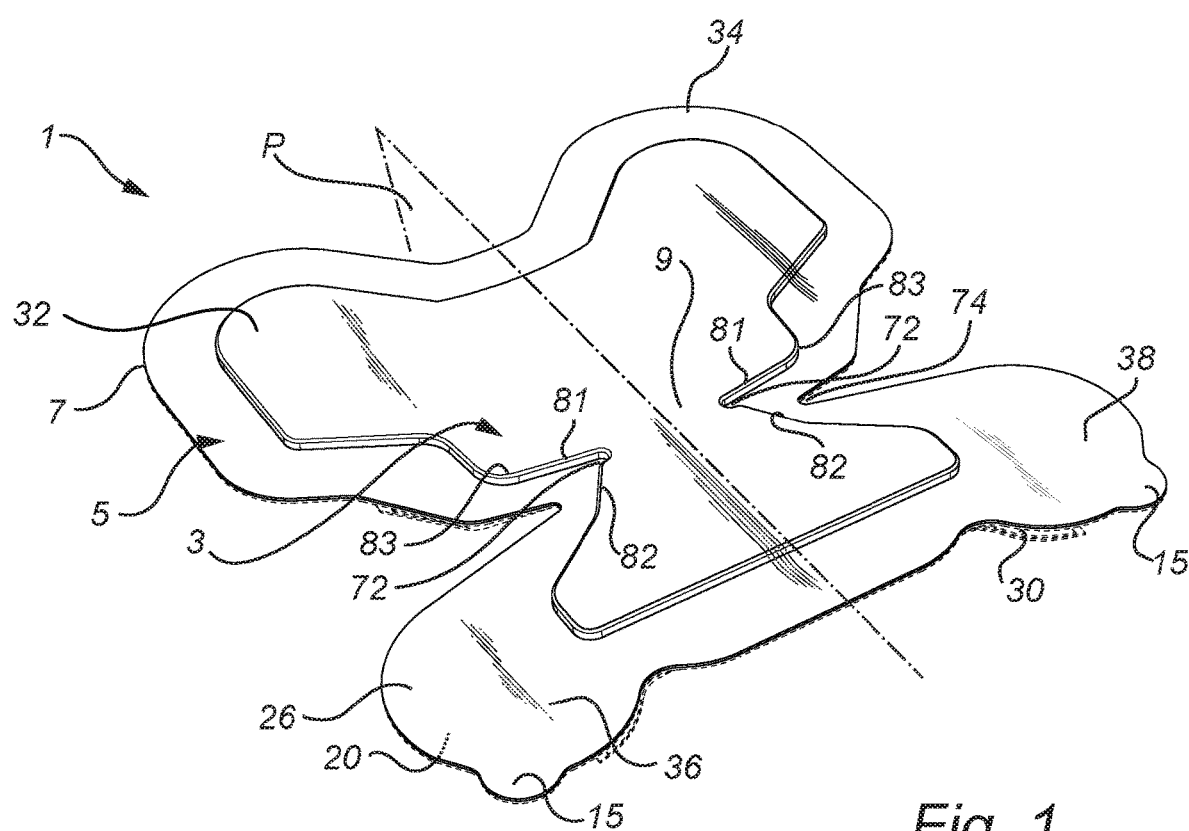
FIG. 1 is a perspective view of a medical dressing according to at least one exemplary embodiment of this disclosure.
Figure 2:
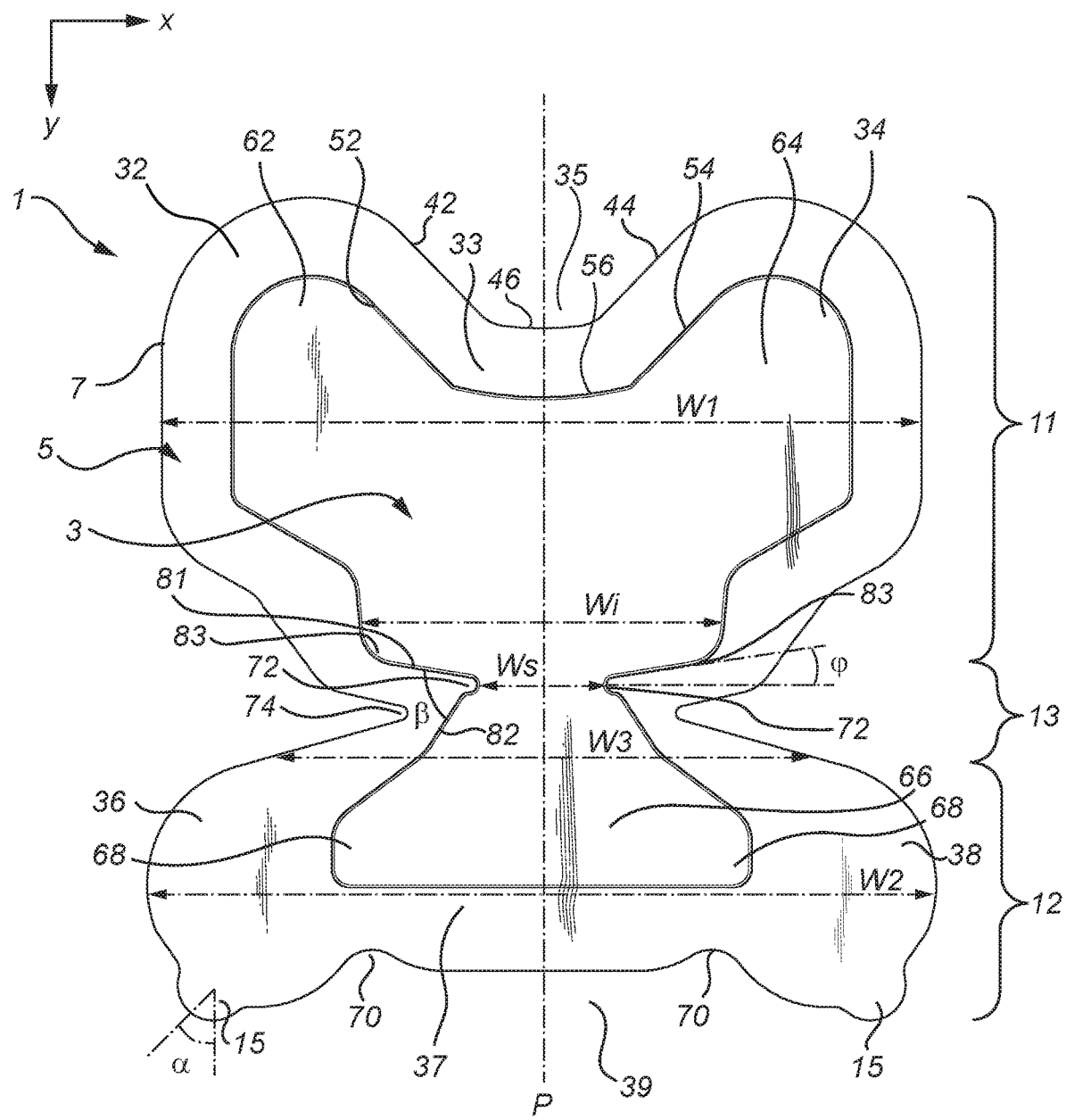
FIG. 2 is a top plan view of the medical dressing illustrated in FIG. 1.

FIGS. 1 and 2 illustrate a medical dressing 1 according to at least one exemplary embodiment of this disclosure. Although the medical dressing 1 may be applied to various areas of the human body, the illustrated embodiment is particularly suitable for application onto a heel for pressure ulcer prevention/mitigation.

The medical dressing 1 comprises a pad 3 which, in its applied state, is intended to cover an area of the human body (such as the heel) where development of pressure ulcer may occur. The pad 3 is a preventive measure, which reduces the risk of pressure ulcers developing at the area covered by the pad 3. The pad 3 is, therefore, suitably made of a pressure relieving material, such as materials exemplified previously in this specification.

The pad 3 is surrounded by a substantially planar border portion 5 extending along the contour of the pad 3. The border portion 5 will thereby form a peripheral edge 7 of the medical dressing 1. In the present illustration, the border portion 5 forms a closed curve around the pad 3, however, it should be understood that in other embodiments the border portion 5 may be interrupted along the contour of the pad 3, such as at the narrowest area 9 of the pad 3.

The contour of the illustrated medical dressing 1 resembles a butterfly-shape, wherein the medical dressing 1 has a first portion 11 having a first width W1, a second portion 12 having a second width W2, and a third portion 13 having a third width W3. The above-mentioned narrowest area 9 of the pad 1 is located at the third portion 13 of the medical dressing 1. If the medical dressing 1 lacks border portion at the third portion 13, then the material of the pad 3 should be suitably sealed, such as by welding to avoid loss of pad material. In the present example the first width W1 is the maximum width of the first portion 11, the second width W2 is the maximum width of the second portion 12, and the third width W3 is the maximum width of the third portion. The third width W3 is smaller than each one of the first width W1 and the second width W2.

The pad 3 has a geometrical plane of symmetry P, i.e. the part of the pad 3 on one side of the plane of symmetry P is mirrored by the part on the other side of the plane of symmetry P. In the illustrated embodiment, the border portion 5 shares the same plane of symmetry P, and so does the entire medical dressing 1. The first, second and third widths W1, W2, W3 extend in a direction which is perpendicular to the plane of symmetry P. This direction may also be referred to as a lateral direction (or in Cartesian coordinates it could e.g. be an x-direction). The medical dressing 1 also extends in the longitudinal direction (in Cartesian coordinates it could e.g. be a y-direction) which coincides and is parallel with the plane of symmetry. The x and y coordinates have been indicated in FIG. 2.

The medical dressing 1 comprises two gripping tabs 15 which are coplanar with the border portion 5 and which project outwardly from the border portion 5. It should be noted that in embodiments in which one of the gripping tabs 15 is omitted, the unchanged pad 3 will still have the plane of symmetry P, but the entire medical dressing 1 will no longer share this (unless the only gripping tab is located along the plane of symmetry of the pad). In the illustrated embodiment, the gripping tabs 15 are located at the second portion 12; however, as explained previously in this disclosure, the gripping tabs 15 may be distributed in a number of different ways. In the illustrated embodiments no other part of the medical dressing 1 extends beyond the gripping tabs 15, as seen in the longitudinal extension of the medical dressing 1 (i.e. as seen in the y-direction).

Each one of the first, second and third widths W1, W2, W3 extends from a respective point of the peripheral edge 7 on one side of the plane of symmetry P to a respective point of the peripheral edge on the other side of the plane of symmetry P, and wherein each one of the first, second and third widths W1, W2, W3 extends perpendicularly to the plane of symmetry P. The third portion 13 is located between and adjoining to the first portion 11 and the second portion 12, and it should be noted that the third width W3 is smaller than each one of the first width W1 and the second width W2.

The first width, W1, may be in the range of from 16 to 25 cm, e.g. from 20 to 22 cm. The second width, W2, may be in the range of from 17 to 26 cm, e.g. from 21 to 23 cm. The third width, W3, may be in the range of from 12 to 17 cm, e.g. from 13 to 15 cm.

Although the illustrated embodiment has a butterfly-shape, it should be understood that other shapes having a narrower central third portion 13 and wider adjoining first and second portions 11, 12 are also conceivable. The general inventive concept is based on the combination of providing the medical dressing with such a narrower central third portion as well as with at least one gripping tab, which results in a medical dressing that is easily detachable and re-applicable, even for challenging body areas such as the heel.

The illustrated medical dressing 1 has an adhesive body contact layer 20, which is adapted to be in contact with the skin. Distally of the body contact layer, the medical dressing has a backing layer 26. The pad 3 is arranged between the backing layer 26 and the body contact layer 20. The radial extension of the pad 3 is smaller than the radial extension of the backing layer 26 and the body contact layer 20. Thus, the backing layer 26 and the body contact layer 20 extend beyond the periphery of the pad 3 to define the border portion 5, which extends along the contour of the pad 3.

Figure 3:
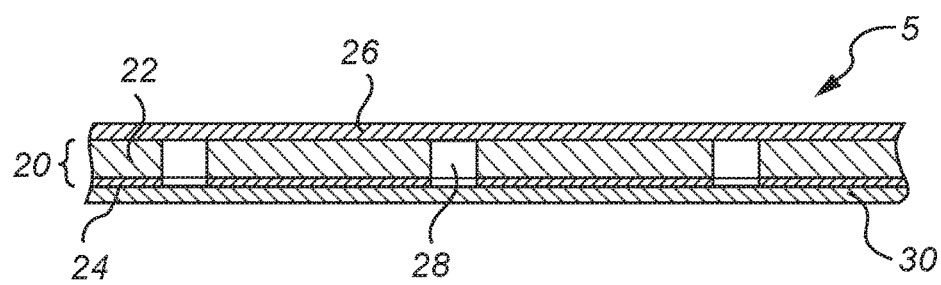
FIG. 3 is a detailed view of the medical dressing illustrated in FIGS. 1 and 2.

FIG. 3 is a detailed view of the medical dressing 1 illustrated in FIGS. 1 and 2, showing a cross-sectional view of the border portion 5 of the medical dressing 1. As can be seen in FIG. 3, the body contact layer 20 includes a film 22 which on its proximal side is coated with an adhesive layer 24. As mentioned above, the backing layer 26 defines the border portion 5 together with the body contact layer 20, and as seen in the figure, the backing layer 26 is attached to the distal side of the film 24. Although the body contact layer 20 may suitably extend across the entire medical dressing 1, it is conceivable to have other embodiments in which the body contact layer 20 is only present at the border portion 5, or present at the border portion 5 and only extending partly across the pad 3. In other words, in some exemplary embodiments, the pad 3 may be in direct contact with areas of the human body.

As can be seen in FIG. 3, the body contact layer 20 (i.e. the film 22 combined with the adhesive layer 24) may suitably be provided with perforations 28 so as to allow moisture to be transported away from the skin. Suitably, the pad 3 may comprise an absorbent material (for instance, distributed in one or more layers of the pad) for absorbing moisture that has travelled through the perforations 28.

FIG. 3 also illustrates a proximally arranged release liner 30 (also indicated in FIG. 1) for protecting the adhesive layer 24 of the body contact layer 20. The medical dressing 1 may be provided with one or more such release liners. The one or more release liners is/are removed before or during application of the medical dressing onto an area of the human body.

Suitably, the adhesive layer 24 covers at least 75% of the surface of the film 22. Therefore, the one or more release liners 30 will suitably cover at least the corresponding area. In some exemplary embodiments, the entire proximal surface of the film 22 is coated with an adhesive layer 24, in which case the one or more release liners 30 will extend across the entire proximal side of the body contact layer (see, for instance, FIGS. 4a and 4b in which five release liners 30a-30e are provided to cover the entire proximal side of the body contact layer 20).

Turning back to FIGS. 1 and 2, the gripping tabs 15 are herein illustrated as being made in one piece with the border portion 5, which may be beneficial from a manufacturing perspective. However, in at least some exemplary embodiments the one or more gripping tabs 15 of the medical dressing 1 may be made from a different (or same) material and attached to the border portion 5. A function of the one or more gripping tabs 15 is to provide a visual indication or guidance to the nursing staff, so that they will know where to start detaching the border portion 5 from the skin in order to allow for visual inspection of the condition of the body area underneath the pad 3. As such, each gripping tab 15, although presenting a relatively small surface area, distinctly projects from the border portion 5. The gripping tab or tabs 15 projecting from the border portion 5 may suitably have a surface area of between 0.4 and 6 cm$^2$, suitably between 1 and 3 cm$^2$. The size of the tab is of course dependent on the size of the dressing. The tab should be of a size that guides the user to see it, and to grasp it properly for inspection.

In the illustrated butterfly-shaped medical dressing 1, the first portion 11 forms a first pair of wings 32, 34 and the second portion 12 forms a second pair of wings 36, 38. Each one of the first and second pairs has one wing (32 and 36, respectively) on one side of the plane of symmetry P and another wing (34 and 38, respectively) on the other side of the plane of symmetry P. There is one gripping tab 15 on each wing of the second pair of wings 36, 38. As previously explained in this application, other gripping tab distributions are also conceivable. For instance, two additional gripping tabs may be added, one for each one of the wings of the first pair of wings 32, 34.

If the medical dressing 1 would be inscribed or placed in a rectangle so that the four wings 32, 34, 36, 38 would be located as closely as possible to the respective four corners of the rectangle, then the gripping tabs 15 would point substantially diagonally relative to the rectangle. This is reflected in at least one exemplary embodiment, according to which the at least one gripping tab 15 projects from the border portion 5 obliquely relative to the plane of symmetry P, i.e. neither parallel nor perpendicular to the plane of symmetry P. Suitably, the at least one gripping tab 15 may project from the border portion at an angle α of 20°-70°, such as 30°-60° relative to the plane of symmetry P.

As best seen in FIG. 2, the contour of the border portion 5 follows a substantially U-shaped path from one of the wings 32 of the first pair of wings to the other one of the wings 34 of the first pair of wings. The legs 42, 44 of the U-shaped path extend obliquely to the plane of symmetry P, while the interconnecting part 46 of the U-shaped path extends substantially perpendicularly to the plane of symmetry P.

In the first portion 11 of the medical dressing 1 the U-shaped path of the border portion is mimicked by the pad 3 which has a co-extending U-shaped path defined by two legs 52, 54 of the U-shape and an interconnecting part 56.

While this disclosure mainly discusses a plane of symmetry of the pad P, it should be understood that the pad 3 also has a geometrical axis of symmetry coinciding with the plane of symmetry P. Thus, the line of symmetry P indicated in the top plan view of FIG. 2 is representative of both the plane of symmetry and the axis of symmetry.

The second portion 12 of the medical dressing 1 comprises an intermediate portion 37 which extends from one (36) of the wings of the second pair of wings across the plane of symmetry P, to the other one (38) of the wings of the second pair of wings. As seen in the axial direction (i.e. direction of axis of symmetry or directions parallel to the axis of symmetry), each one of the wings 36, 38 of the second pair of wings extends beyond the intermediate portion 37. That is, the wings 36, 38 extend further away from the first and third portions 11, 13 than the intermediate portion 37. This results in a void 39 being present between the second pair of wings 36, 38 (seen in a direction perpendicular to the plane of symmetry P). A similar configuration can be the to be present in the first portion 11 of the medical dressing 1 as well, since the first pair of wings 32, 34 extend beyond an intermediate portion 33 in the first portion 11 of the dressing 1, thereby creating a void 35, i.e. the space between the legs 42, 44 of the U-shaped path of the border portion 5.

The above-mentioned U-shaped paths 42, 44, 46, 52, 54, 56 as well as the configuration of the extending wings 36, 38 in the second portion 12 facilitate the folding and conforming of the medical dressing 1 to a heel. The illustrated configuration is further beneficial in that the lateral parts 62, 64 of the pad 3 (which form part of the first of wings 32, 34, respectively) are adapted to cover the malleoli of the heel, which may otherwise be at risk of developing pressure ulcers (e.g. if a person lies in a bed on his/her side rather than on his/her back). From the third portion 13 of the medical dressing a substantially triangular shaped pad portion 66 extends into the second portion 12 of the medical dressing 1. The substantially triangular shape is truncated at the third portion 13 of the medical dressing 1 and is suitably provided with rounded or non-sharp corner pieces 68 in the second portion 12. In the applied state of the medical dressing 1 the rounded corner pieces 68 of the second portion 12 will be folded up from the sole of the foot to cover the lateral heel edge (illustrated in FIG. 5), which is also an area where pressure ulcers have a tendency to develop.

Continuing with FIG. 2, it may be noted that in the illustrated embodiment and in other exemplary embodiments, the peripheral edge 7 of the border portion at the second portion 12 of the dressing may have the following configuration. The peripheral edge 7 at each one of the wings 36, 38 of the second pair of wings may transit from the wing to the intermediate portion 37 via a respective concavity 70 in the peripheral edge 7. This too facilitates the folding and handling of the medical dressing 1 during application and/or re-application (after visual inspection of the relevant body area).

Turning now to the narrowest area 9 of the pad, on each side of the plane of symmetry the pad 3 is provided with a respective wedge-shaped indentation 72 between the first portion 11 of the dressing and the second portion 12 of the dressing 1. The smallest width Ws of the pad 3 at the narrowest area 9 may suitably be in the range of 3-4.5 cm. At a distance of 1 cm from the smallest width Ws of the pad 3, the pad 3 has an increased width Wi in the first portion 11. The increase in width, i.e. (Wi−Ws)/Ws is in the range of 100%-300%, suitably in the range of 150%-250%.

The wedge-shaped indentations 72 form the waist of the pad 3 at the third portion 13 of the medical dressing 1. A similar waist is formed also in the border portion 5 by corresponding wedge-shaped indentations 74. As seen in FIG. 2, the wedge-shaped indentations 72 of the pad 3 may be slightly displaced relative to the wedge-shaped indentations 74 of the border portion 5, so that the wedge-shaped indentations 72 of the pad 3 is located more towards the first portion 11 of the medical dressing 1, while the wedge-shaped indentations 74 of the border portion 5 is located more towards the second portion 12 of the medical dressing 1. This allows for a good application of the border portion 5 around a heel.

In the illustrated embodiment, and also in other exemplary embodiments, each wedge-shaped indentation 72 of the pad 3 may be at least partly formed by a first substantially linear rim portion 81 extending from the third portion 13 of the medical dressing 1 to the first portion 11 of the medical dressing 1 and a second substantially linear rim portion 82 extending from the third portion 13 of the medical dressing 1 to the second portion 12 of the medical dressing 1. An angle β of 50°-70°, suitably 55°-65°, may be formed between the directions of extension of the first and second substantially linear rim portions 81, 82.

An imaginary geometric line may be drawn between the first and second substantially linear rim portions 81, 82, wherein the imaginary geometric line extends perpendicularly to the plane of symmetry. Relative to such an imaginary geometric line, each first substantially linear rim portion 81 forms an angle φ of 0°-20°. This relatively small or no angle φ has been found to provide a good fit of the pad 3 around a heel. The outer ends 83 of the first substantially linear rim portions may be separated from one another by a distance of 9-16 cm, suitably 10-12 cm.

FIGS. 4a-4g illustrate a procedure for applying the medical dressing illustrated in FIGS. 1 and 2 onto a heel. It should be noted that for the illustrated embodiment, the perforated body contact layer 20 extends across the entire proximal side of the medical dressing. Thus, there are perforations present both at the central part covering the pad and at the border portions. However, for the sake of clarity, in FIGS. 4a-4g, the perforations have not been indicated at the central part of the body contact layer which covers the pad; the perforations 28 have only been indicated at the border portion.

Figure 4A:
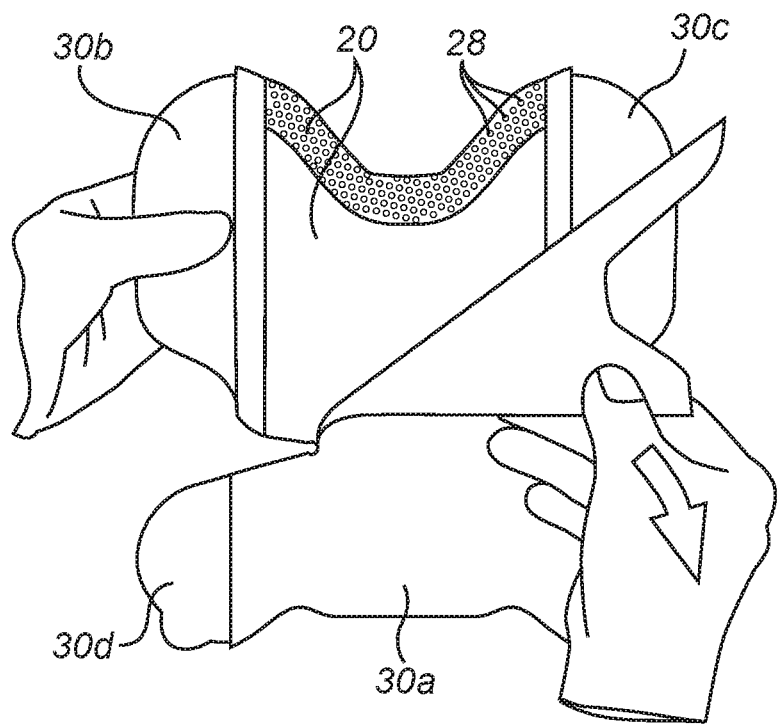
FIGS. 4a-4g illustrate a procedure for applying the medical dressing illustrated in FIGS. 1 and 2 onto a heel.
Figure 4B:
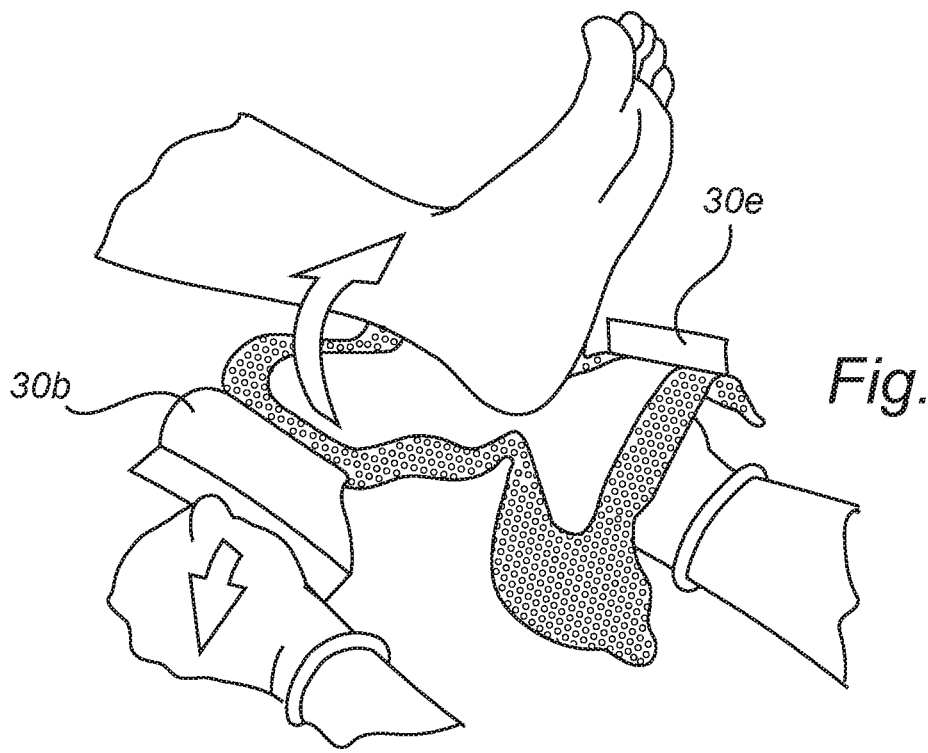
Figure 4C:
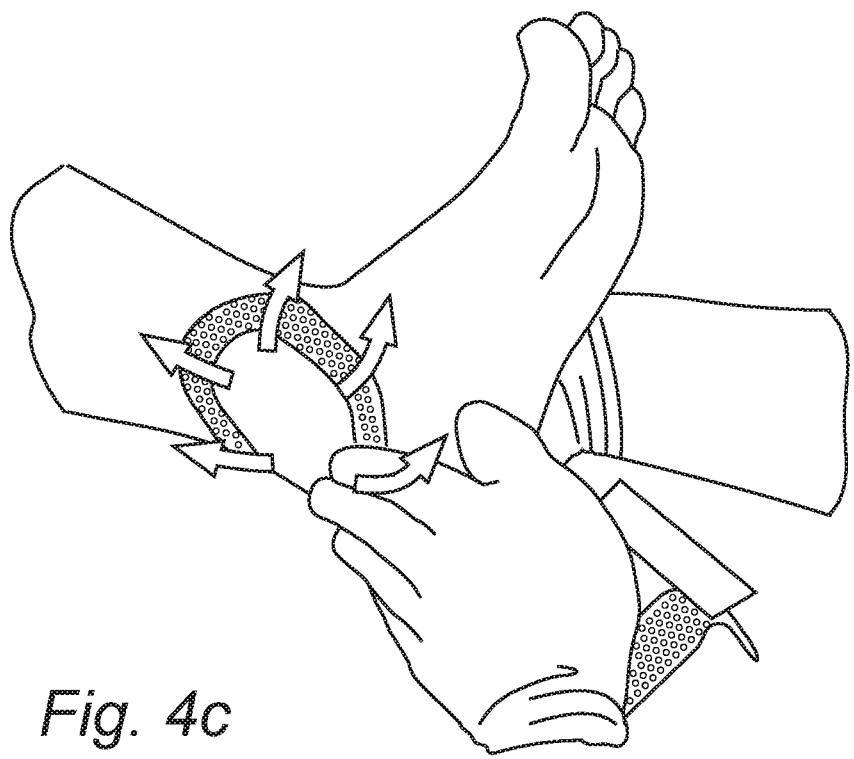
Figure 4D:
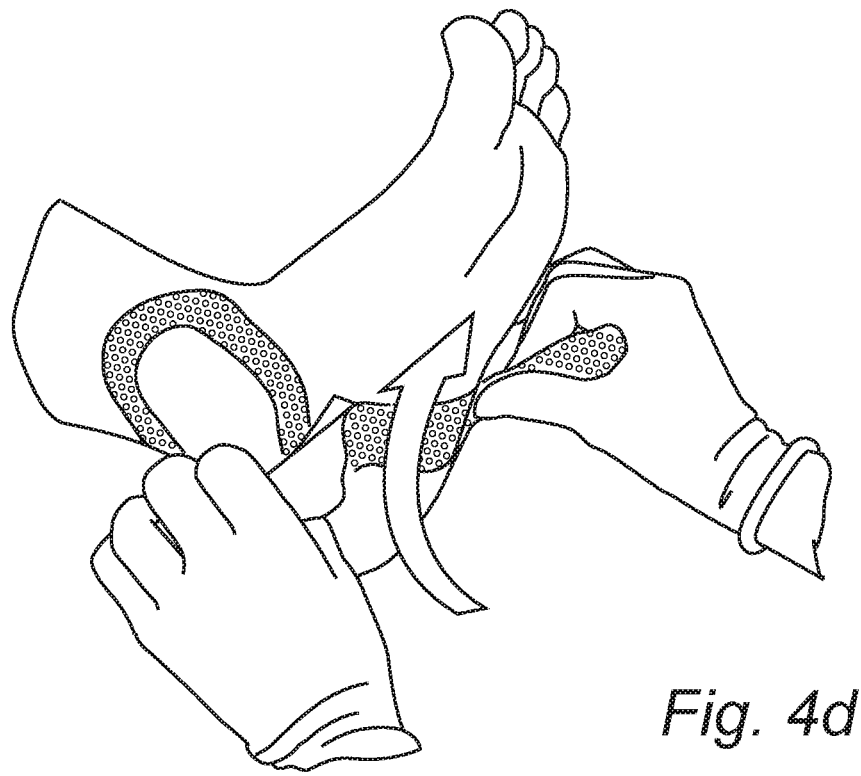
Figure 4E:
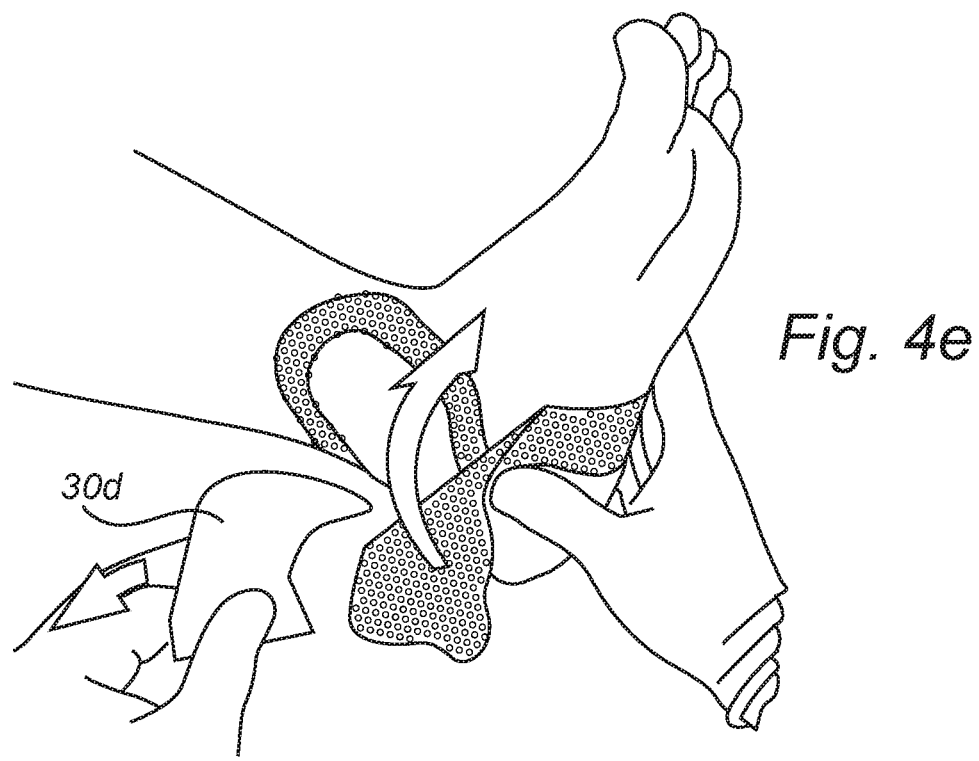
Figure 4F:
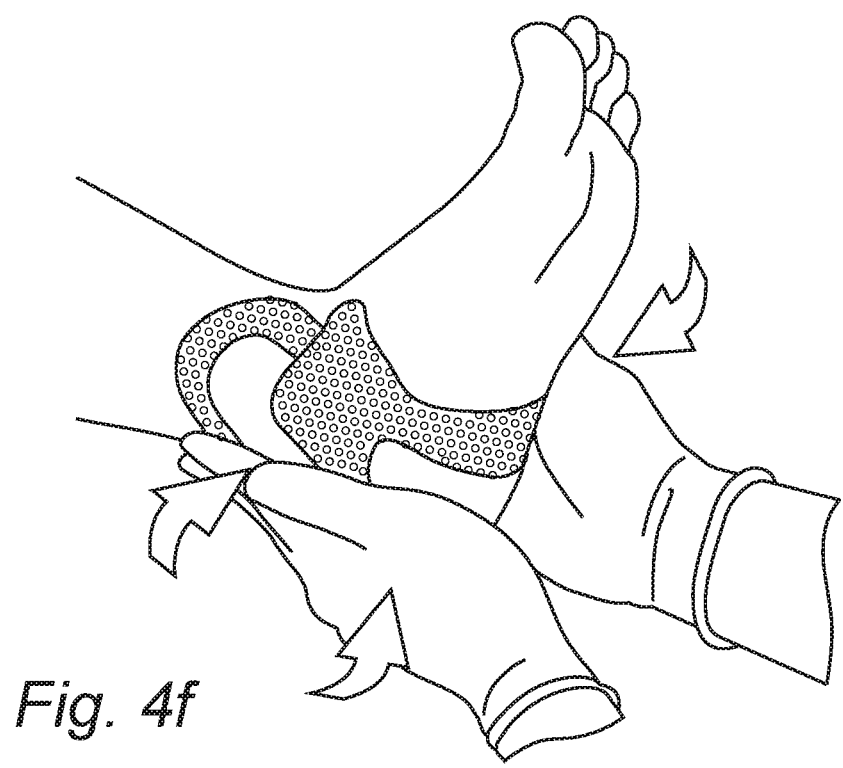
Figure 4G:
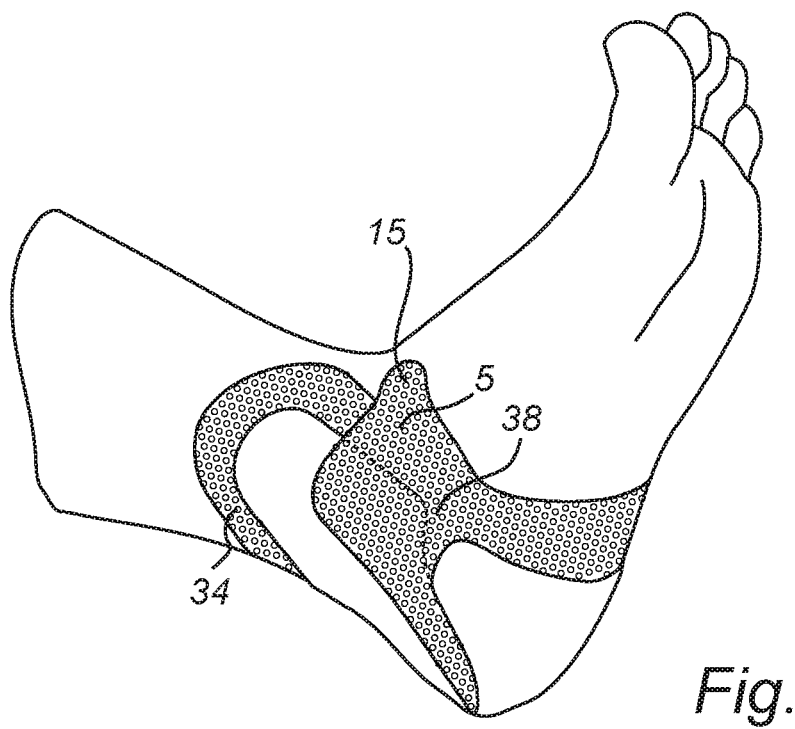

Starting with FIG. 4a, it may be noted that in the illustrated embodiment, there are provided five release liners 30a-30e (four of which, 30a-30d being visible), namely one central release liner 30a and four wing release liners 30b-30d. The central release liner 30a is removed first, revealing the proximal side of the perforated adhesive body contact layer 20. In FIG. 4b, the revealed part of the body contact layer is applied to the back of the heel, the two wing release liner portions 30b, 30c at the first portion of the medical dressing are removed and the first pair of wings is folded up to the lateral sides of the foot, in particular so that the pad will cover the malleoli. In FIG. 4c, the border portion at the first portion of the dressing is applied and is smoothed in different directions to avoid or reduce the number of wrinkles in the border portion. In FIG. 4d, the second portion of the dressing is folded towards the sole of the foot and in FIG. 4e the two wing release liner 30d, 30e at the second portion of the dressing are removed so that the second pair of wings may be folded up over the lateral edges of the heel. In FIG. 4f, the border portion of the second portion of medical dressing is smoothed in different directions. FIG. 4g illustrates the final applied state, from which can be deducted that the second pair of wings 36, 38 partly overlap the first pair of wings 32, 34. The gripping tab 15, however, distinctly projects from the border portion 5 and the rest of the medical dressing and provides a clear indication to the nursing staff for where to start removing the dressing for visual inspection of the heel, when it is desired to check the condition of the skin at the heel.

It should be noted that instead of having five release liners 30a-30e as illustrated in FIGS. 4a-4b, the illustrated medical dressing (and other embodiments) may have a different number of release liners. For instance, in some exemplary embodiments the number of release liners may be three. In other exemplary embodiments the number of release liners may be more than five, such as for instance six release liners.

Figure 5:
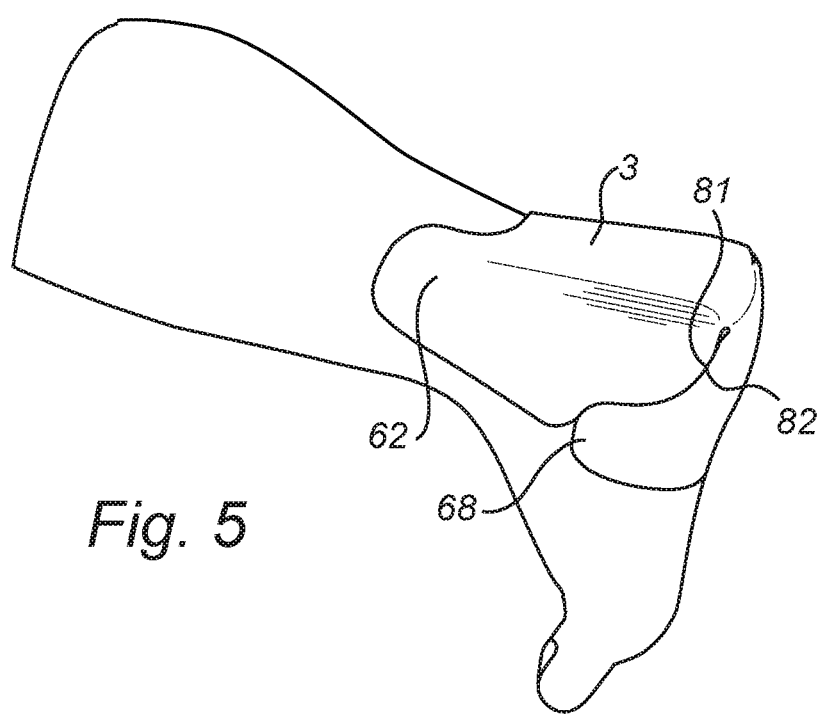
FIG. 5 only illustrates the pad of the medical dressing in FIGS. 1 and 2, and its configuration when applied onto a heel.

In FIG. 5, for sake of clarity and for explanatory reasons, only the actual pad 3 is shown. The lateral parts 62, 64 of the pad 3 at the first pair of wings cover the malleoli. The corner pieces 66, 68 at the second portion of the medical dressing cover the heel edge. The angle β and/or φ (see FIG. 2) between the first substantially linear rim portion 81 and the second substantially linear rim portion 82 is such that in the applied state, the rim portions 81, 82 may abut each other, thereby avoiding any gap around the heel.

The invention claimed is:

1. A medical dressing, comprising:
a pad having a geometrical plane of symmetry and a pad contour edge,
a substantially planar border portion extending along the contour edge of the pad, the border portion forming a closed curve, uninterrupted peripheral edge around an entirety of the pad contour edge, wherein the medical dressing comprises:
a first portion having a first width,
a second portion having a second width, and
a third portion having a third width,
wherein each one of the first, second and third widths extends from a respective point of the peripheral edge on one side of the plane of symmetry to a respective point of the peripheral edge on the other side of the plane of symmetry, and wherein each one of the first, second and third widths extends perpendicularly to the plane of symmetry,
wherein the third portion is located between and adjoining to the first portion and the second portion,
wherein the third width is smaller than each one of the first width and the second width,
wherein the second portion of the medical dressing comprises a first wing on one side of the plane of symmetry and a second wing on the other side of the plane of symmetry, the first wing comprising a first gripping tab that is integral with and projects outwardly from the border portion of the first wing, the second wing comprising a second gripping tab that is integral with and projects outwardly from the border portion of the second wing, such that the border portion extends uninterrupted from the pad edge to the first and second gripping tabs; and
an adhesive body contact layer adapted to be in contact with the skin in use, the first and second gripping tabs being covered by the adhesive body contact layer such that the first and second gripping tabs are adhered to patient skin in use.

2. The medical dressing of claim 1, wherein the medical dressing has a longitudinal extension in a longitudinal direction coinciding and running in parallel with the geometrical plane of symmetry, and a lateral extension in a lateral direction running perpendicularly to the geometrical plane of symmetry, wherein at least one of the first and second gripping tabs projects from the border portion at least in the longitudinal direction so that no other part of the medical dressing extends beyond the at least one gripping tab in the longitudinal direction.

3. The medical dressing of claim 1, further comprising a backing layer,
wherein the pad is arranged between the backing layer and the adhesive body contact layer, wherein the backing layer and the adhesive body contact layer extend beyond the periphery of the pad to define the border portion, which extends along the contour of the pad.

4. The medical dressing of claim 3, wherein the adhesive body contact layer comprises a film coated with an adhesive layer, wherein the adhesive layer covers at least 75% of the surface of the film.

5. The medical dressing of claim 3, wherein the border portion has a bending length of at least 32 mm as measured by a standard test method.

6. The medical dressing of claim 1, wherein the first and second gripping tabs are made in one piece with the border portion.

7. The medical dressing of claim 1, wherein on each side of the plane of symmetry, the pad is provided with a respective wedge-shaped indentation between the first portion of the dressing and the second portion of the dressing, forming a waist of the pad at the third portion of the dressing.

8. The medical dressing of claim 1, wherein, on each side of the plane of symmetry, the pad has a first substantially linear rim portion extending from the third portion of the dressing to the first portion of the dressing and a second substantially linear rim portion extending from the third portion of the dressing to the second portion of the dressing.

9. The medical dressing of claim 8, wherein an angle of 50°-70°, is formed between directions of extension of the first and second substantially linear rim portions.

10. The medical dressing of claim 8, wherein an angle of 0°-20° is formed between a direction of extension of the first substantially linear rim portion and an imaginary geometric line, the imaginary geometric line extending between the first and second substantially linear rim portions and extending perpendicularly to the plane of symmetry.

11. The medical dressing of claims 8, wherein on each side of the plane of symmetry, each one of the first substantially linear rim portions has an inner end located closest to the plane of symmetry and an outer end located farthest from the plane of symmetry, wherein the outer end of the first substantially linear rim portion on one side of the plane of symmetry and the outer end of the first substantially linear rim portion on the other side of the plane of symmetry are separated from one another by a distance of 9-16 cm.

12. The medical dressing of claim 11, wherein the pad has a smallest width in a direction perpendicular to the plane of symmetry, the smallest width being in the range of 3-4.5 cm.

13. The medical dressing of claim 1, wherein the medical dressing is substantially butterfly wing-shaped, with the first portion forming a first pair of wings, the second portion forming a second pair of wings, wherein each one of the first and second pairs has one wing on one side of the plane of symmetry and another wing on the other side of the plane of symmetry.

14. The medical dressing of claim 13, wherein the contour of the border portion follows a substantially U-shaped path from one of the wings of the first pair of wings to the other one of the wings of the first pair of wings.

15. The medical dressing of claim 12, wherein the dressing comprises a first pair of wings and a second pair of wings, wherein the pad has a geometrical axis of symmetry coinciding with the plane of symmetry, the axis of symmetry defining an axial direction, wherein the second portion of the dressing comprises an intermediate portion which extends from one of the wings of the second pair of wings, across the plane of symmetry, to the other one of the wings of the second pair of wings,
wherein, seen in the axial direction, each one of the wings of the second pair of wings extends beyond the intermediate portion such that in a direction perpendicular to the plane of symmetry, a void is present between the second pair of wings.

16. The medical dressing of claim 12, wherein the dressing comprises a first pair of wings and a second pair of wings, wherein the first gripping tab projects outwardly from the border portion of one of the wings of the second pair of wings, wherein the second gripping tab projects outwardly from the border portion of the other one of the second pair of wings.

17. The medical dressing of claim 3, comprising a tensile strength of between 3.5 and 10 N at an elongation of 25%.

18. The medical dressing of claim 3, comprising a tensile strength of between 4 and 6 N at an elongation of 25%.

19. A medical dressing, comprising:
- a pad having an outer contour, the pad comprising an upper portion with first and second extending wings with a U-shaped path between first and second extending wings, and a lower portion having a substantially triangular shape,
- a border portion extending along the outer contour of the pad, the border portion forming a peripheral edge around the pad, wherein the border portion comprises a butterfly-shape with:
  - an upper portion having first and second extending wings with a U-shaped path between first and second extending wings, wherein the upper portion of the border has a peripheral edge that mimics by shape the outer contour of the upper portion of the pad;
  - a middle narrowed waist portion defined by wedge-shaped indentations in both the pad and the border; and
  - a lower portion having first and second wings, wherein the lower portion of the border has a peripheral edge that does not directly mimic by shape the outer contour of the lower portion of the pad.

20. The medical dressing of claim 19, wherein the lower portion of the border comprises first and second gripping tabs extending from first and second wings of the lower portion.

21. The medical dressing of claim 19, wherein the lower portion of the border comprises first and second concavities that define lobes of the first and second wings.

* * * * *